US00PP11458P

United States Patent [19]

Fell

[11] Patent Number: Plant 11,458

[45] Date of Patent: Jul. 25, 2000

[54] AGLAONEMA PLANT NAMED '001CKF'

[75] Inventor: David Fell, Hilo, Hi.

[73] Assignee: Hawaiian Sunshine Nursery, Inc., Hilo, Hi.

[21] Appl. No.: 08/748,513

[22] Filed: Nov. 8, 1996

[51] Int. Cl.[7] ..... A01H 5/00

[52] U.S. Cl. ..... Plt./88.1

[58] Field of Search ..... Plt./88.1

*Primary Examiner*—Elizabeth C. Kemmerer

*Attorney, Agent, or Firm*—Driggs, Lucas, Brubaker & Hogg Co., L.P.A.

[57] ABSTRACT

There is disclosed a representative plant of Aglaonema designated "001CKF", which is one displaying variegated foliage consisting of two colors on the top leaf surface, comprising green and silver extensive from the leaf margins to the midrib in irregular sizes and patterns but appearing as alternating stripes following the pattern of the veins and a green-white petiole; and a bottom surface that is a lighter green than the green of the top surface with small green-white spots scattered throughout which are faintly visible on the top surface; and having a vigorous growth habit and a cold resistance.

1 Drawing Sheet

BACKGROUND OF THE DISCLOSURE

This invention relates to Aglaonema Plants and, more particularly, to a cultivar thereof which is one of a series from a long, detailed program for developing such plants. This program for the development of Aglaonema has been carried on in the vacinity of Hilo, Hi., and the particular seedling of this invention is a result of cross between the seed parent *Aglaonema nitidum* 'Curtisii' and the pollen parent of an unnamed Aglaonema similar to a variety called 'Manila Whirl'. The detailed description of the plant enables the identification of the plant without regard to specific botanical statements, since the plant is clearly identifiable by reason of its certain peculiar differences as distinguished from prior existing Aglaonema. This new variety of Aglaonema was asexually reproduced by tissue culture near Apopka, Fla. and such reproduction has shown this new variety to come true in successive generations. This propagation of the new variety by tissue culture in the usual controlled environment clearly discloses the continued maintenance of the characteristics described herein which distinguish this new variety from the parent variety and other related varieties.

SUMMARY OF THE INVENTION

The plant was selected based on its unique and distinctive foliar variegation and stem coloration along with its trait for greater resistance to the cold than other known Aglaonema such as 'Silver King' or 'Silver Queen'. The top surfaces of the leaves consist of a two color variegation of green and silver. The green and silver colors are extensive from the leaf margins to the midrib in generally irregular patterns and sizes but appearing as alternating stripes following the pattern of the veins. On the top surface the midrib is green from the base up almost the entire length of the leaf with the uppermost portion being silver. The bottom surfaces of the leaves are also green but lighter than the top surfaces with the midrib being green- white for almost the entire length of the leaf with the uppermost portion changing to the green of the rest of the bottom surface. The bottom surfaces of the leaves also exhibit small green-white spots that are faintly visible in the top surface of the leaves. The petiole color is a green-white, while the stem is generally not visible due to clasping nature of the petioles.

DESCRIPTION OF THE DRAWINGS

This new variety of Aglaonema is illustrated by the accompanying photographic drawings and depicts the plant by the best possible color representaion using color photography.

BOTANICAL DESCRIPTION OF THE PLANT

Figure 1:
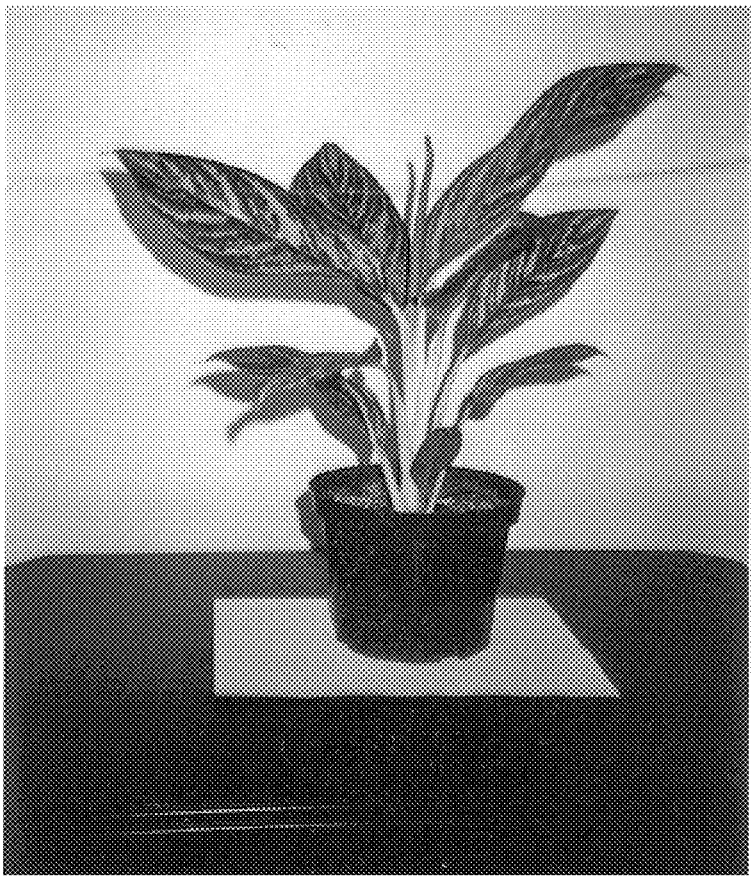
FIG. 1 is a color photographic print showing a frontal view of the plant.
Figure 2:
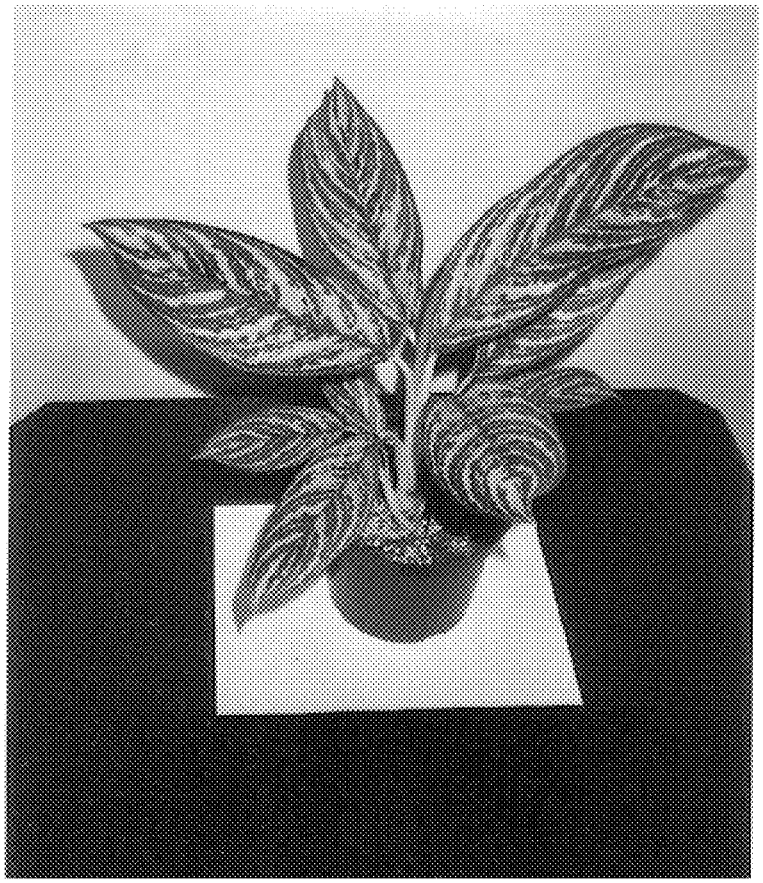
FIG. 2 is a color photographic print showing a top angled perspective view of the plant.

All color references below are measured against The Royal Horticultural Society Colour Chart. Colors are approximate as color depends on horticultural practices such as light level and fertilization rate, among others.

Parentage:

*Seedling.*—Seed parent—*Aglaonema nitidum* 'Curtisii'. Pollen parent—Aglaonema sp. unnamed.

Asexually reproduced by cutting and tissue culture.

Flower:

*Blooming habit.*—Intermittent; flower color: exterior exhibits a field of 144A moderating side-to-side to 144B yellow-green with spots of 145D in an irregular pattern thereon; interior is 145C, yellow-green.

Foliage: One leaflet, large in size, and abundant.

*New foliage color.*—Top Surface—137A and 190B Green and silver variegated, with bottom surface spots faintly visible. Bottom Surface—138A, with small spots of 157B scattered throughout.

*Shape.*—Elliptic.

*Texture.*—Leathery.

*Ribs and veins.*—Ordinary and impressed.

*Edge.*—Smooth.

*Petiole.*—Color 157B Based on the third expanded leaf from the terminal on a terminal that had flowered previously: the petiole wings measure about 8 mm wide at the mid point of a cross section of the petiole, the cross section was taken mid way between the leaf blade and the base of the petiole; the wings extend from the base of the petiole to within 3 cm of the base of the blade, more of less depending upon the growing conditions of the plant; the wings form a circle with the side facing the stem open, approximately 70 degrees; the petiole follows the stem axis but diverges from the axis approximately 9–12 cm from the leaf base forming an acute angle with the axis of the stem; petiole length is about 22–24 cm. Under side is smooth.

*Stipules.*—None.

*Ovaries.*—All enclosed in calyx. Sterile with its own pollen.

*Axillary breaks.*—When grown from tissue cultured liners for approximately 9 months plants averaged 5 breaks with one leaf expanded; leaves show true color pattern with the first open leaf.

Plant:

*Form.*—Bush.

*Growth.*—Very vigorous, rapid growing; plants propagated from tissue cultured 72 cell trays liners were shifted into 6" pots and grown for approximately 9 months; at that time they reached salable size in 5–7 canes per pot.

*Height.*—Approximate measurements of average—Undetermined Spread—28" to 36".

*Hardiness.*—Cold resistant.

I claim:

1. A new and distinct variety of Aglaonema as shown and described, characterized particularly as to novelty by the attractive and distinct variegated foliage consisting of two colors on the top leaf surface, comprising green and silver extensive from the leaf margins to the midrib in irregular patterns appearing as alternating stripes following the pattern of the veins, a bottom leaf surface of green with small green-white spots scattered throughout and being faintly visible on said top surface, a green-white petiole and being cold resistant.

* * * * *